(12) United States Patent
Kostrzewski et al.

(10) Patent No.: US 10,004,562 B2
(45) Date of Patent: Jun. 26, 2018

(54) SURGICAL INSTRUMENT HOLDER FOR USE WITH A ROBOTIC SURGICAL SYSTEM

(71) Applicant: KB Medical SA, Lausanne (CH)

(72) Inventors: Szymon Kostrzewski, Lausanne (CH); Billy Nussbaumer, Boudry (CH)

(73) Assignee: Globus Medical, Inc., Audubon, PA (US)

( * ) Notice: Subject to any disclaimer, the term of this patent is extended or adjusted under 35 U.S.C. 154(b) by 669 days.

(21) Appl. No.: 14/695,154

(22) Filed: Apr. 24, 2015

(65) Prior Publication Data

US 2015/0305817 A1 Oct. 29, 2015

Related U.S. Application Data

(60) Provisional application No. 61/983,816, filed on Apr. 24, 2014.

(51) Int. Cl.
| | |
|---|---|
| *B25B 1/22* | (2006.01) |
| *A61B 19/00* | (2006.01) |
| *A61B 34/00* | (2016.01) |
| *A61B 34/30* | (2016.01) |
| *A61B 17/00* | (2006.01) |
| *A61B 90/00* | (2016.01) |

(52) U.S. Cl.
CPC .......... *A61B 19/2203* (2013.01); *A61B 34/30* (2016.02); *A61B 34/70* (2016.02); *A61B 2017/00464* (2013.01); *A61B 2017/00477* (2013.01); *A61B 2090/3983* (2016.02)

(58) Field of Classification Search
USPC .............................................. 269/71, 72, 73
See application file for complete search history.

(56) References Cited

U.S. PATENT DOCUMENTS

| | | | |
|---|---|---|---|
| 4,166,602 | A | 9/1979 | Nilsen et al. |
| 4,799,779 | A | 1/1989 | Mesmer |
| 5,408,409 | A | 4/1995 | Glassman et al. |
| 5,948,002 | A | 9/1999 | Bonutti |
| D435,107 | S | 12/2000 | Blair et al. |
| D456,080 | S | 4/2002 | Karlsson |

(Continued)

FOREIGN PATENT DOCUMENTS

| | | |
|---|---|---|
| DE | 10003051 A1 | 8/2001 |
| EP | 1693011 A1 | 8/2006 |

(Continued)

OTHER PUBLICATIONS

ROSA Is a New Stereotactic Neurological Surgery Robot, Neurological Surgery, Jun. 13, 2011 (http://www.medgadget.com/2011/06/rosa-neuro-surgery-robot.html).

(Continued)

*Primary Examiner* — Joseph J Hail
*Assistant Examiner* — Shantese McDonald

(57) ABSTRACT

Described herein is a surgical instrument holder for use with a robotic surgical system, for example, during spinal surgery. In certain embodiments, the surgical instrument holder is an interface between the robotic arm and a surgical instrument used during surgery. This interface may hold the surgical instrument precisely, rigidly, and in a stable manner while permitting a surgeon to easily and quickly install or withdraw the instrument in case of emergency.

17 Claims, 16 Drawing Sheets

(56) References Cited

U.S. PATENT DOCUMENTS

| | | |
|---|---|---|
| D461,484 S | 8/2002 | Kraft |
| 6,451,027 B1 | 9/2002 | Cooper et al. |
| 6,604,021 B2 | 8/2003 | Imai et al. |
| D506,257 S | 6/2005 | Smith |
| D528,216 S | 9/2006 | Korner |
| 7,155,316 B2 | 12/2006 | Sutherland et al. |
| 7,196,454 B2 | 3/2007 | Baur et al. |
| D548,759 S | 8/2007 | Kraft |
| D553,655 S | 10/2007 | Jennings et al. |
| D572,739 S | 7/2008 | Jennings et al. |
| D646,703 S | 10/2011 | Wong |
| D654,503 S | 2/2012 | Sapper |
| D655,324 S | 3/2012 | Wong |
| D660,845 S | 5/2012 | Schmauch et al. |
| D679,016 S | 3/2013 | Jarva |
| D685,479 S | 7/2013 | Charles |
| 8,509,503 B2 | 8/2013 | Nahum et al. |
| D690,421 S | 9/2013 | Charles |
| D692,139 S | 10/2013 | Charles |
| D702,841 S | 4/2014 | Wyrozub |
| D708,332 S | 7/2014 | Kim |
| D724,738 S | 3/2015 | Dorris et al. |
| 9,125,680 B2 | 9/2015 | Kostrzewski et al. |
| 2003/0097060 A1 | 5/2003 | Yanof et al. |
| 2004/0034282 A1 | 2/2004 | Quaid |
| 2004/0128026 A1 | 7/2004 | Harris et al. |
| 2004/0143168 A1 | 7/2004 | Hu et al. |
| 2005/0245817 A1 | 11/2005 | Clayton et al. |
| 2006/0036264 A1 | 2/2006 | Selover et al. |
| 2006/0142657 A1 | 6/2006 | Quaid et al. |
| 2006/0161136 A1* | 7/2006 | Anderson .............. A61B 90/57 606/1 |
| 2006/0161138 A1 | 7/2006 | Orban et al. |
| 2007/0005189 A1 | 1/2007 | Furubo |
| 2007/0032906 A1 | 2/2007 | Sutherland et al. |
| 2007/0055291 A1 | 3/2007 | Birkmeyer et al. |
| 2007/0119123 A1 | 5/2007 | Clark et al. |
| 2007/0156157 A1 | 7/2007 | Nahum et al. |
| 2007/0270685 A1 | 11/2007 | Kang et al. |
| 2008/0215181 A1 | 9/2008 | Smith et al. |
| 2008/0221520 A1 | 9/2008 | Nagel et al. |
| 2008/0287862 A1 | 11/2008 | Weitzner et al. |
| 2009/0088848 A1 | 4/2009 | Martz et al. |
| 2009/0326318 A1 | 12/2009 | Tognaccini et al. |
| 2010/0166496 A1 | 7/2010 | Bennett et al. |
| 2010/0192720 A1 | 8/2010 | Helmer et al. |
| 2010/0210939 A1 | 8/2010 | Hartmann et al. |
| 2010/0319713 A1 | 12/2010 | Byers et al. |
| 2011/0082462 A1 | 4/2011 | Suarez et al. |
| 2011/0087238 A1 | 4/2011 | Wang et al. |
| 2011/0126844 A1 | 6/2011 | Cinquin et al. |
| 2011/0190789 A1 | 8/2011 | Thiran et al. |
| 2012/0059378 A1 | 3/2012 | Farrell |
| 2013/0081636 A1 | 4/2013 | Schuele |
| 2013/0113798 A1 | 5/2013 | Nahum et al. |
| 2013/0172902 A1 | 7/2013 | Lightcap et al. |
| 2013/0317344 A1 | 11/2013 | Borus et al. |
| 2014/0052151 A1* | 2/2014 | Hingwe ................. A61B 34/30 606/130 |
| 2014/0066944 A1* | 3/2014 | Taylor ................. B25J 15/0466 606/103 |
| 2014/0121676 A1 | 5/2014 | Kostrzewski et al. |
| 2015/0032164 A1 | 1/2015 | Crawford et al. |
| 2015/0045764 A1 | 2/2015 | Kaplan et al. |
| 2015/0045813 A1 | 2/2015 | Kostrzewski et al. |
| 2015/0100066 A1 | 4/2015 | Kostrzewski et al. |
| 2015/0196365 A1 | 7/2015 | Kostrzewski et al. |
| 2015/0202009 A1 | 7/2015 | Nussbaumer et al. |
| 2015/0223897 A1 | 8/2015 | Kostrzewski et al. |

FOREIGN PATENT DOCUMENTS

| | | |
|---|---|---|
| WO | WO-98/02107 A1 | 1/1998 |
| WO | WO-2004/014244 A2 | 2/2004 |
| WO | WO-2005/122916 A1 | 12/2005 |
| WO | WO-2006/091494 A1 | 8/2006 |
| WO | WO-2007/136768 A2 | 11/2007 |
| WO | WO-2008/097540 A2 | 8/2008 |
| WO | WO-2009/013406 A2 | 1/2009 |
| WO | WO-2012/131660 A1 | 10/2012 |
| WO | WO-2012/133912 A1 | 10/2012 |
| WO | WO-2013/079843 A1 | 6/2013 |
| WO | WO-2013/098496 A1 | 7/2013 |
| WO | WO-2013/160239 A1 | 10/2013 |
| WO | WO-2013/192598 A1 | 12/2013 |
| WO | WO-2015/049109 A1 | 4/2015 |
| WO | WO-2015/107099 A1 | 7/2015 |
| WO | WO-2015/110542 A1 | 7/2015 |
| WO | WO-2015/121311 A1 | 8/2015 |
| WO | WO-2015/162256 A1 | 10/2015 |

OTHER PUBLICATIONS

Zemiti, N. et al., A new Robot for Force Control in Minimally Invasive Surgery, Proceedings of 2004 IEEE/RSJ International Conference on Intelligent Robots and Systems, 4:3643-3648 (2004).

International Search Report, PCT/EP2015/058913, 4 pages, dated Jul. 6, 2015.

Written Opinion, PCT/EP2015/058913, 6 pages, dated Jul. 6, 2015.

* cited by examiner

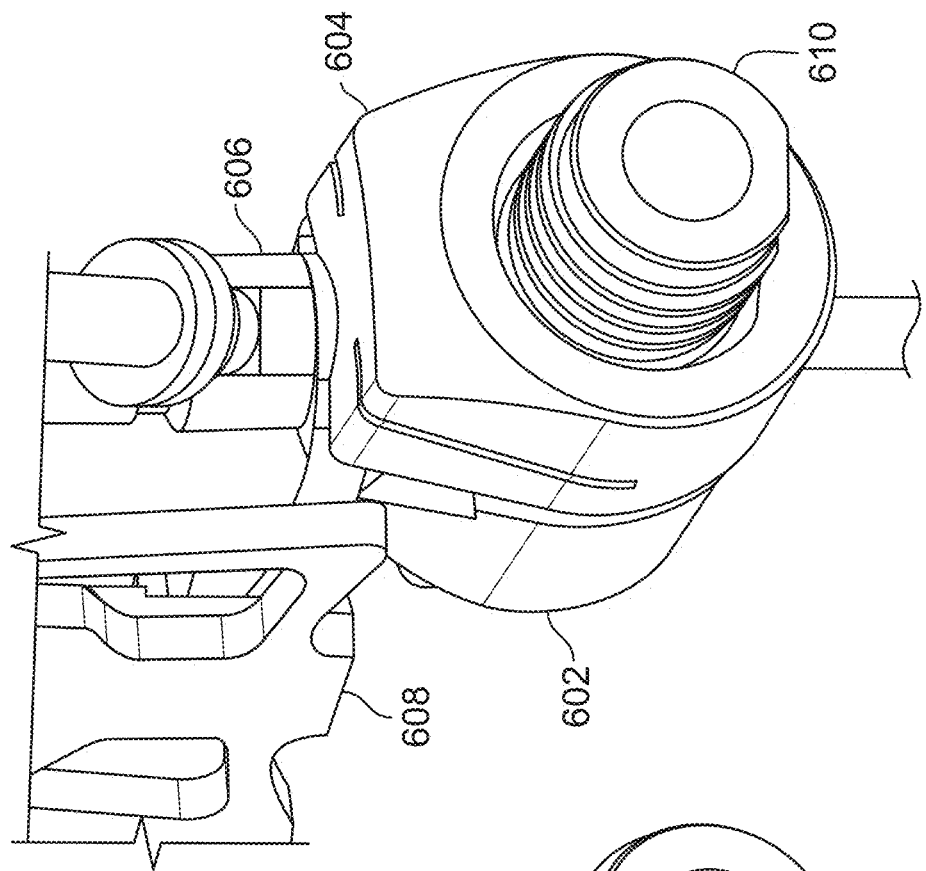
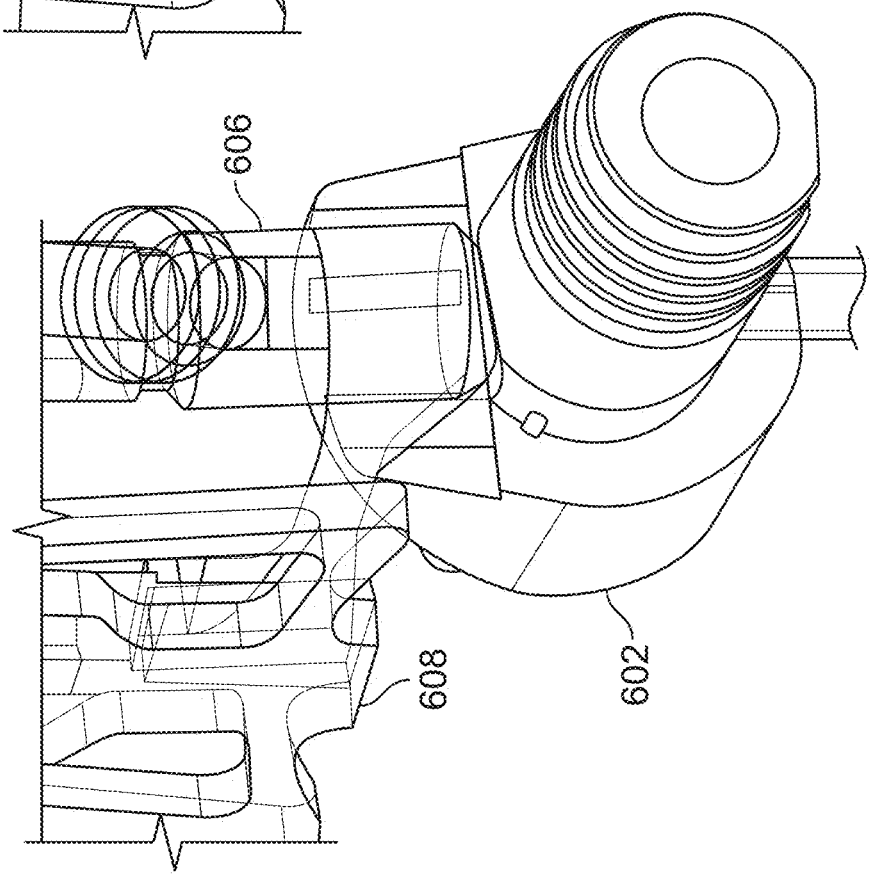
FIG. 6A
FIG. 6B

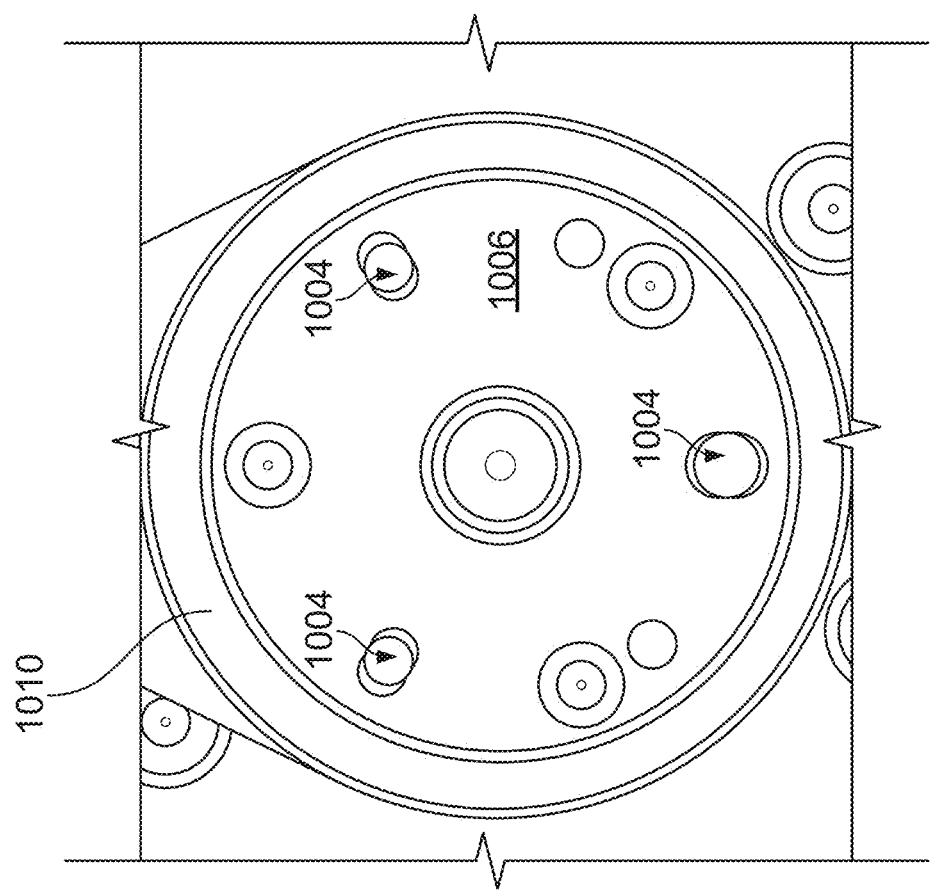

SURGICAL INSTRUMENT HOLDER FOR USE WITH A ROBOTIC SURGICAL SYSTEM

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeons field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading. Thus, there is a need for a system for stabilizing surgical instruments while allowing the instruments and the instrument holder to be both easily sterilized and installed and removed from the robotic system without deteriorating localization precision as well as attachment rigidity.

SUMMARY

Described herein is a surgical instrument holder for use with a robotic surgical system, for example, during spinal surgery. In certain embodiments, the holder is attached to a robotic arm and provides a rigid structure that allows for precise preparation of patient tissue (e.g., preparation of a pedicle) by drilling, tapping, or other manipulation, as well as precise placement of a screw in a drilled hole or affixation of a prosthetic or implant in a prepared patient situation.

In certain embodiments, the surgical instrument holder is an interface between the robotic arm and a surgical instrument used during surgery. The surgical instrument holder holds the surgical instrument precisely, rigidly, and in a stable manner while permitting a surgeon to easily and quickly install or withdraw the instrument in case of emergency. The surgical instrument includes a base that is mechanically coupled to the robotic arm.

In some implementations, the instrument holder needs to be sterilized (e.g., in autoclave). The disclosed instrument holder may be easily installed and removed from the robotic system without deteriorating localization precision as well as attachment rigidity. Localization precision is achieved by, for example, localization pins inserted into the base. The pins may come in contact with oblong openings in a thin localization plate precisely held on the robotic arm. The instrument holder's base is localized on the robotic arm using pins that come in contact with oblong openings in the localization plate. A screw may be tightened directly into the robot to rigidly attached the instrument holder's base to the robot.

A surgical instrument slides into a channel in the base of the instrument holder. A clamp may be positioned with the instrument between the base and the clamp such that the instrument is securely held between the base and the clamp when a nut is tightened against the clamp (e.g., pushing the clamp against the instrument). A navigation marker may also be secured between the base and the clamp. The surface of the clamp that contacts the nut may be cambered such that a horizontal line of contact is formed instead of a full surface. This horizontal line of contact allows the clamp to slightly tilt to accommodate for dimensional variations.

The disclosed technology, in certain embodiments, includes a surgical instrument holder for use with a robotic surgical system. The surgical instrument holder, in certain embodiments, includes a base configured to be mechanically coupled to a robotic arm of the robotic surgical system. The base may include a first channel having an interior surface sized and shaped to accommodate a tightening screw configured to securely attach the base directly or indirectly to a robotic arm of the robotic surgical system, a second channel having an interior surface with a tapered cylindrical shape sized to accommodate a surgical instrument therethrough such that movement of the surgical instrument is constrained in all directions except along an axis defined by the second channel surface, a first tapered curved surface extending along the axis of the second channel configured to be engaged by a surgical instrument when the surgical instrument is secured in the second channel, wherein first channel and the second channel intersect, and one or more pins inserted into the base such that the one or more pins (e.g., three pins), upon mechanically coupling the base to the robotic arm, engage one or more openings (e.g., one or more oblong openings) in a tool support (e.g., in a localization plate of the robotic arm) thereby precisely locating the surgical instrument holder relative to the robotic arm (e.g., where the one or more openings are wider than the one or more pins and the one or more openings taper long their lengths).

The surgical instrument holder, in certain embodiments, includes a clamp configured to engage the surgical instrument when placed through the second channel such that the surgical instrument is securely held between the clamp and the base upon tightening of a nut. The clamp may include a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of the nut, wherein the nut is configured to engage threads on an exterior surface of the first channel and a cambered surface of the clamp. The instrument holder may be configured such that a navigation marker is securely held between the clamp the base upon placing the navigation marker between the clamp and the base and tightening the nut. In certain embodiments, the navigation marker is used by a navigation camera to track the surgical instrument.

An exterior surface of the first channel may be threaded to securely accommodate the nut such that surgical instrument is securely held between the clamp the base upon placing the surgical instrument in the second channel and tightening the nut. In certain embodiments, the surgical instrument is an instrument guide (e.g., drill guide) configured to receive a second surgical instrument therethrough, the second surgical instrument being a drill bit, tap, screw driver, or awl.

In certain embodiments, the base includes a threaded bushing having an interior surface. In certain embodiments, the first channel passes through interior surface of the threaded bushing and the interior surface of the threaded bushing is threaded such that the threads on the tightening screw engage the threads on the threaded bushing as the tightening screw is inserted through the threaded bushing. In certain embodiments, the tightening screw includes a tip on a proximate end of a screw body; a head on a distal end of the screw body; and threads along a portion of the screw body. In certain embodiments, the threads along the portion of the screw body are along a portion of the screw body closest to the tip of the tightening screw. In certain embodiments, the portion of the screw body closest to the head is smooth such that the tightening screw is loosely held in place by the threaded bushing when the tightening screw is fully inserted into the threaded bushing.

In certain embodiments, the disclosed technology includes a surgical instrument holder for use with a robotic surgical system, the surgical instrument holder including: a base configured to be mechanically coupled to a robotic arm of the robotic surgical system, the base including: a first channel having an interior surface sized and shaped to accommodate a tightening screw configured to securely attach the base directly or indirectly to a robotic arm of the robotic surgical system, a second channel having an interior surface with a tapered cylindrical shape sized to accommodate a surgical instrument therethrough such that movement of the surgical instrument is constrained in all directions except along an axis defined by the second channel surface, a first tapered curved surface extending along the axis of the second channel configured to be engaged by a surgical instrument when the surgical instrument is secured in the second channel, wherein first channel and the second channel intersect, and one or more pins inserted into the base such that the one or more pins, upon mechanically coupling the base to the robotic arm, engage one or more openings in a tool support thereby precisely locating the surgical instrument holder relative to the robotic arm; and a clamp configured to engage the surgical instrument when placed through the second channel such that the surgical instrument is securely held between the clamp and the base upon tightening of a nut.

In certain embodiments, the base includes a threaded bushing having an interior surface.

In certain embodiments, the first channel passes through interior surface of the threaded bushing and the interior surface of the threaded bushing is threaded such that the threads on the tightening screw engage the threads on the threaded bushing as the tightening screw is inserted through the threaded bushing.

In certain embodiments, the tightening screw includes: a tip on a proximate end of a screw body; a head on a distal end of the screw body; and threads along a portion of the screw body.

In certain embodiments, the threads along the portion of the screw body are along a portion of the screw body closest to the tip of the tightening screw.

In certain embodiments, the portion of the screw body closest to the head is smooth such that the tightening screw is loosely held in place by the threaded bushing when the tightening screw is fully inserted into the threaded bushing.

In certain embodiments, the clamp includes a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of the nut, wherein the nut is configured to engage threads on an exterior surface of the first channel and a cambered surface of the clamp.

In certain embodiments, the one or more openings are one or more oblong openings.

In certain embodiments, the one or more pins comprise three pins.

In certain embodiments, the surgical instrument is an instrument guide configured to receive a second surgical instrument therethrough, the second surgical instrument comprising a member selected from the group consisting of: a drill bit, tap, screw driver, and awl.

In certain embodiments, the instrument guide is a drill guide.

In certain embodiments, the robotic surgical system is for use in spinal surgery.

In certain embodiments, instrument holder is configured such that a navigation marker is securely held between the clamp the base upon placing the navigation marker between the clamp and the base and tightening the nut.

In certain embodiments, the navigation marker is used by a navigation camera to track the surgical instrument.

In certain embodiments, the tool support is a localization plate of the robotic arm.

In certain embodiments, the one or more openings are wider than the one or more pins and the one or more openings taper long their lengths.

In certain embodiments, an exterior surface of the first channel is threaded to securely accommodate the nut such that surgical instrument is securely held between the clamp the base upon placing the surgical instrument in the second channel and tightening the nut.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 6A is an illustration of an example surgical instrument holder before a clamp is installed;

FIG. 6B is an illustration of an example surgical instrument holder with a clamp inserted and positioned against the instrument;

FIGS. 10A-B are illustrations of a system for securing the instrument holder on the robotic arm;

Figure 1:
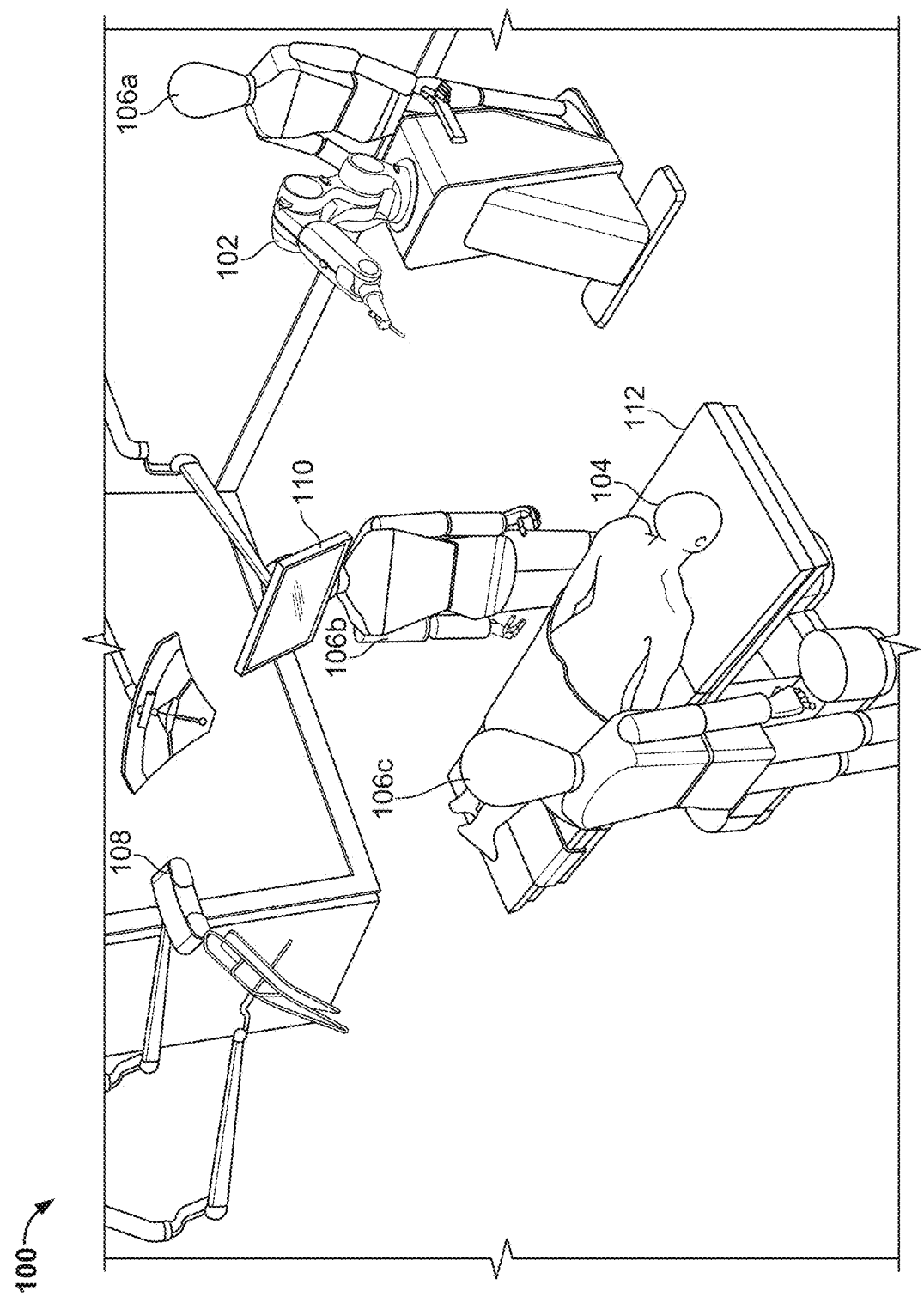
FIG. 1 is an illustration of an example robotic surgical system in an operating room.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

FIG. 1 illustrates an example robotic surgical system in an operating room 100. In some implementations, one or more surgeons, surgical assistants, surgical technologists and/or other technicians, (106a-c) perform an operation on a patient 104 using a robotic-assisted surgical system. In the operating room the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization mechanism increases the global stiffness of the mobile cart relative to the floor in order to ensure the accuracy of the surgical procedure. In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector may be a camera, a video camera, an infrared detector, field generator and sensors for electromagnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

Figure 2:
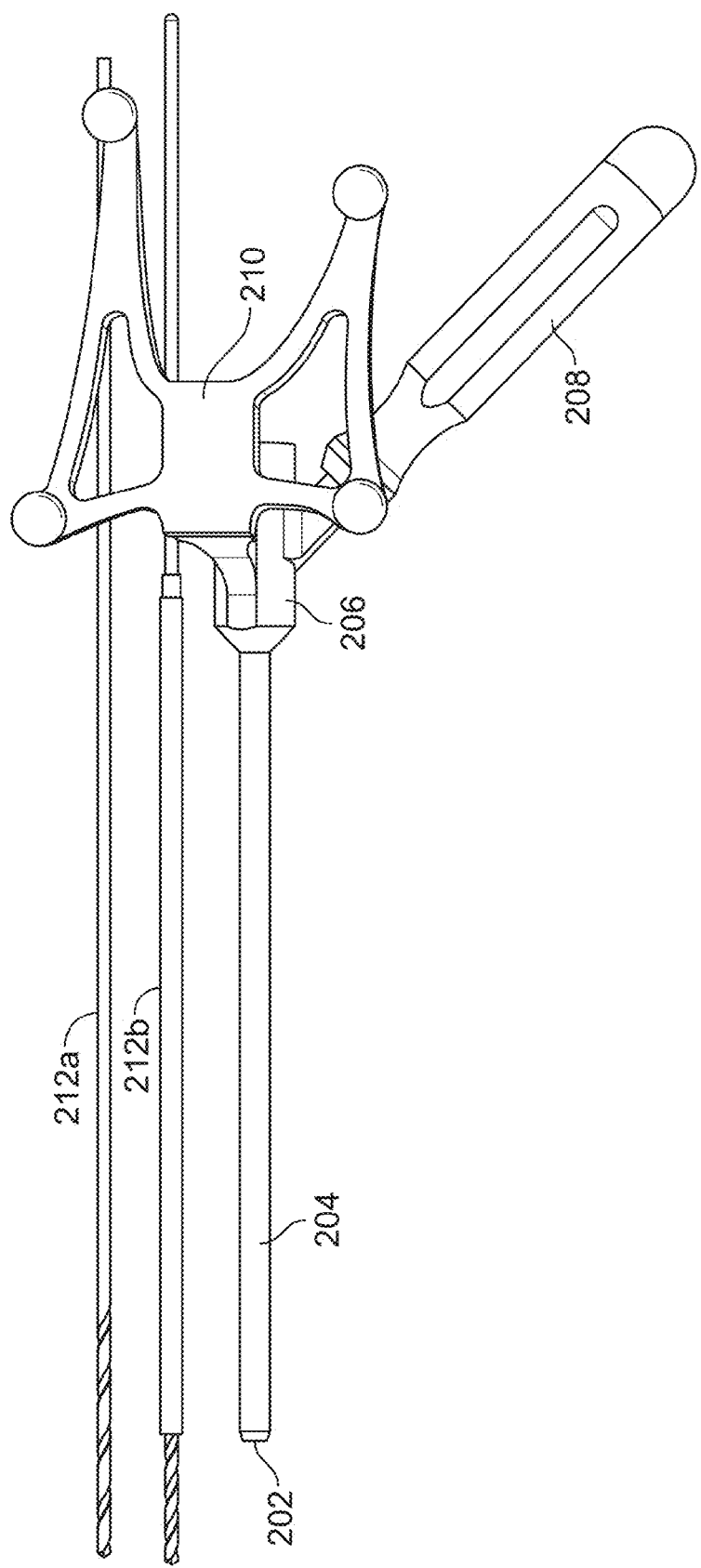
FIG. 2 is an illustration of an example drill guide and two drill bits.

FIG. 2 is an illustration of an example drill guide and two drill bits. In some implementations, the surgical instrument held by the instrument holder is an instrument guide (e.g., drill guide) configured to receive a second surgical instrument therethrough. The second surgical instrument may be a drill bit, tap, screw driver, or awl.

In some implementations, an instrument holder is an interface between the robotic arm and a surgical instrument used during surgery. The instrument holder may be configured to hold the surgical instrument precisely, rigidly, and in a stable manner while permitting a surgeon to easily and quickly install, or withdraw the surgical instrument in case of emergency. The surgical instrument may be an instrument guide such as the drill guide 202 shown in FIG. 2. In this example, the drill guide 202 includes a hollow tube 204 with a reinforcement 206 at one end. A handle 208 and/or a navigation marker 210 may be attached (removably or permanently) to the reinforcement 206. The navigation marker may be, for example, navigation tracker such as the Dedicated NavLock™ tracker from Medtronic, Inc. of Minneapolis, Minn. Drill bits 212a-b may be used with the drill guide 202 to perform an operation, such as preparing holes in vertebrae.

Figure 3A:
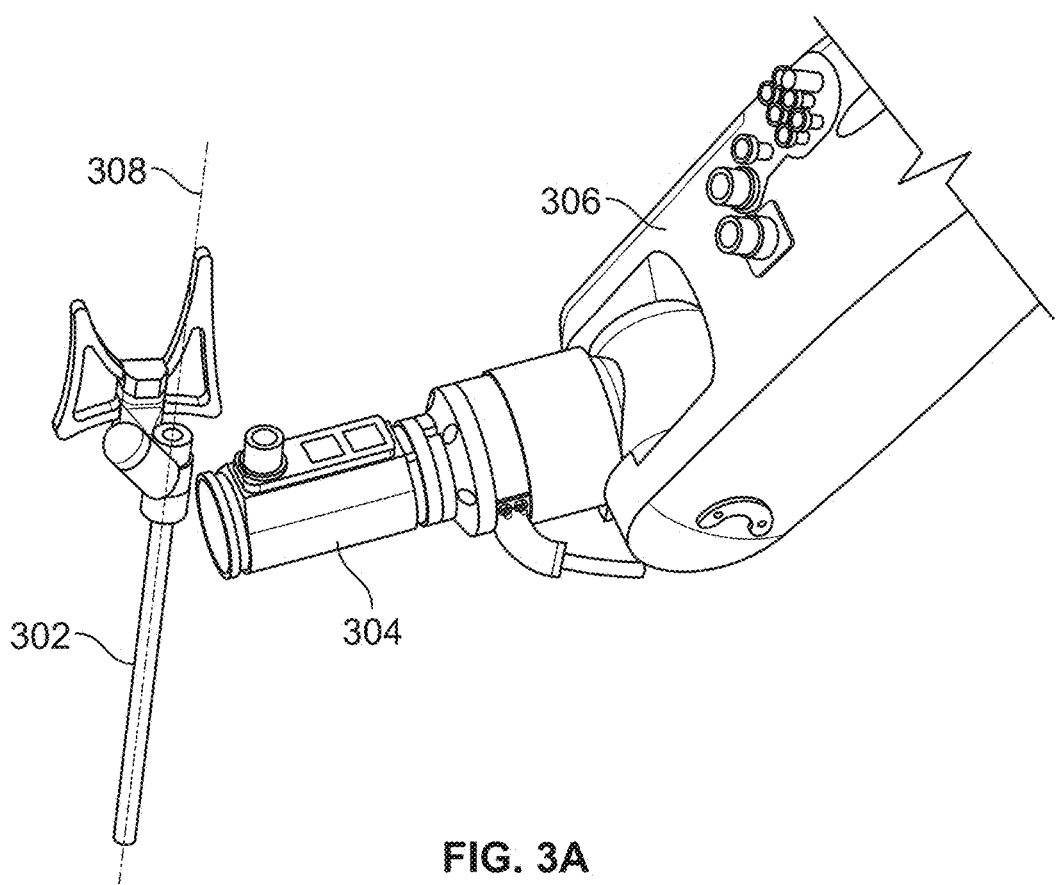
FIG. 3A is an illustration of a drill guide in the position in which it is held relative to the robotic arm.
Figure 3B:
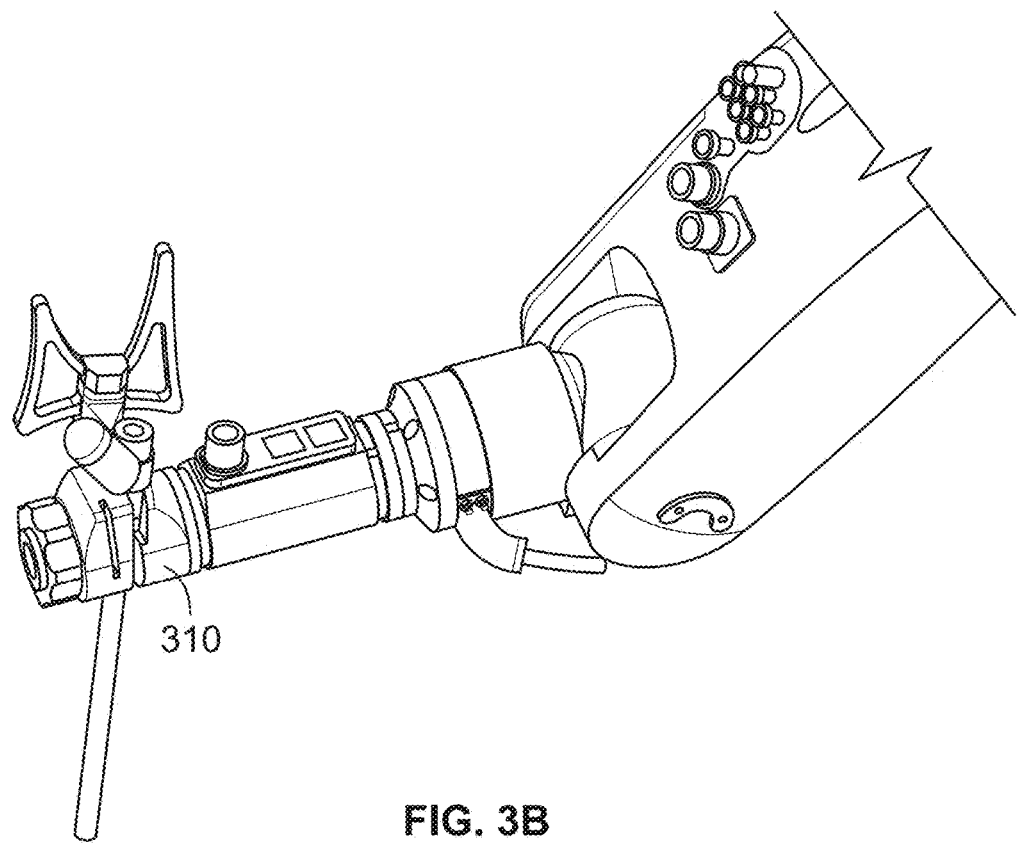
FIG. 3B is an illustration of a drill guide held by an example instrument holder.

FIG. 3A is an illustration of a drill guide 302 in the position in which it is held relative to a tool holder's body 304. The tool holder 304 is attached to the robotic arm 306. The term tool holder is a generic term used to designate, in some implementations, the entire device that is attached to the robot arm's tip. FIG. 3B is an illustration of a drill guide held by an example instrument holder that includes, among other things, a base 310.

Figure 4:
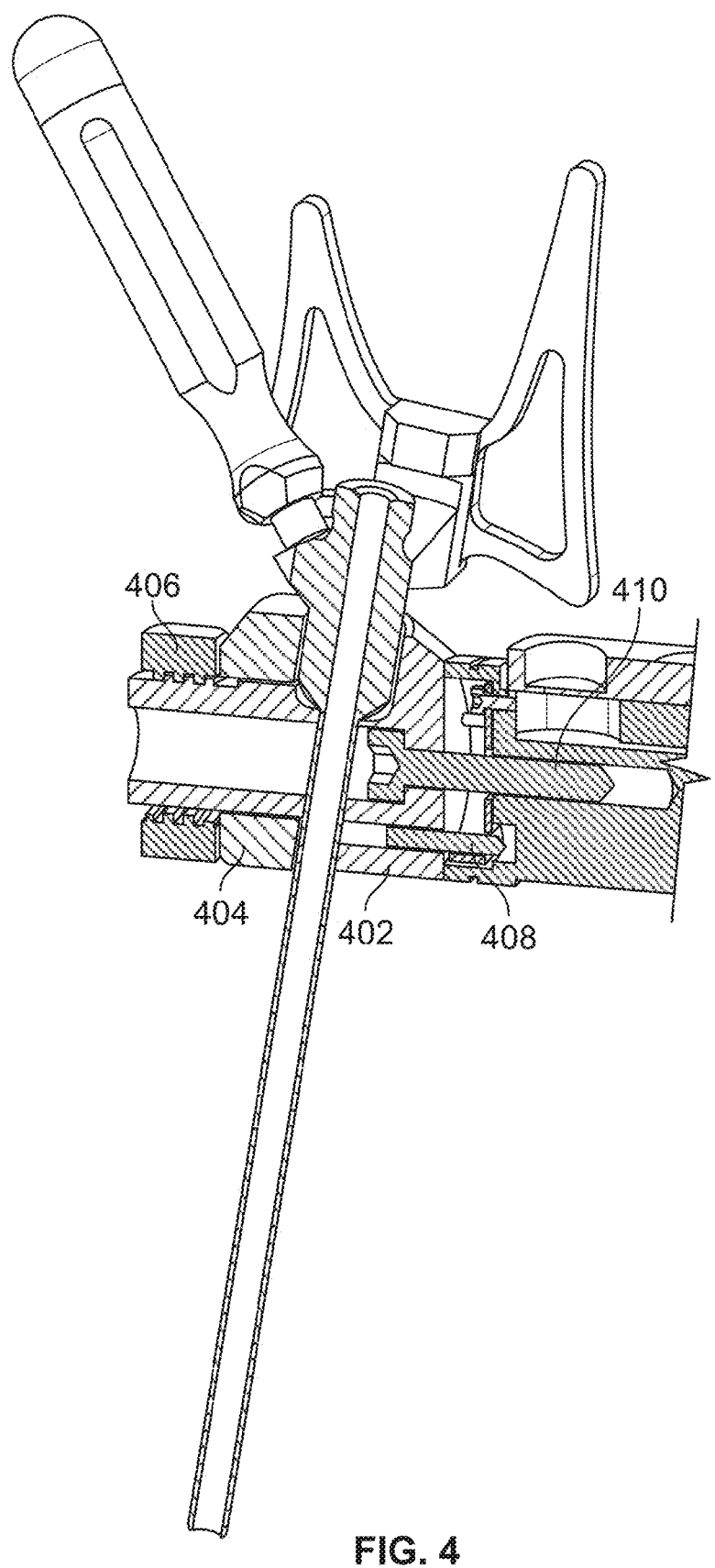
FIG. 4 is an illustration of a cross-sectional view an example instrument holder with a drill guide held therein.

FIG. 4 is an illustration of a cross-sectional view of an example instrument holder with a drill guide held therein. In some implementations, the instrument holder includes a base 402, a clamp 404, a nut 406, localization pins 408 (e.g., three localization pins), and a tightening screw 410. The base 402 is configured to be mechanically coupled to the robotic arm via a screw 410 inserted in a channel of the base 402. The base 402 includes a second channel through which a surgical instrument (e.g., a drill guide) may be placed. The nut 406 may be tightened to securely hold the surgical instrument between the clamp 404 and the base 402.

Figure 5B:
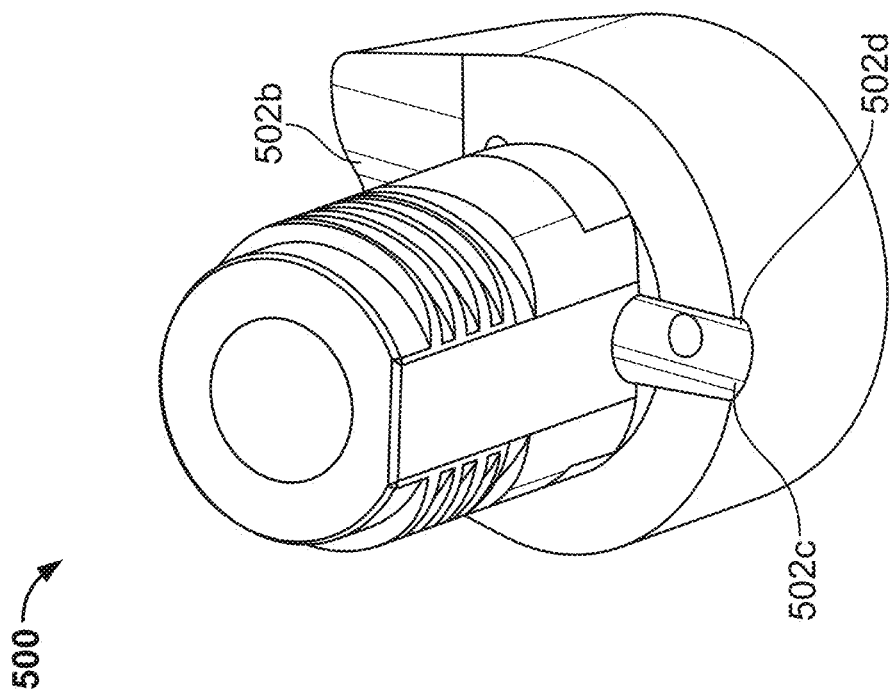
FIGS. 5A-B are illustrations of an example base of a surgical instrument holder.
Figure 5A:
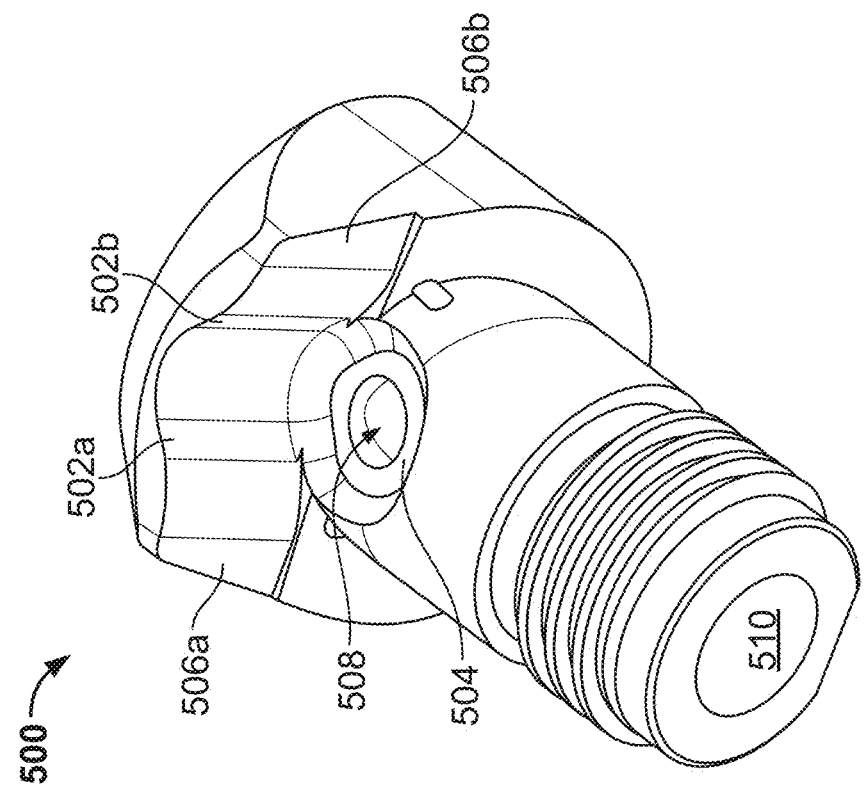

FIGS. 5A-B are illustrations of an example base 500 of a surgical instrument holder. The base may include two surfaces (502a-b) (e.g., forming a large "V"—shown in blue in FIG. 5A) allowing localizing of the instrument guide precisely as well as in a stable manner. The surfaces 502a and 502b may be flat or curved surfaces. The large "V" in the upper portion of the base (e.g., surfaces 502a-b) may receive the cylindrical reinforcement portion of the guide (e.g., 206 in FIG. 2) while another small "V" (shown by 502c-d) receives the external cylindrical tube portion of the guide (e.g., 204 in FIG. 2). Surface 504 may define an axial position of the instrument guide. Surface 506a and/or 506b may come in contact with a navigation marker's attachment mechanism to prevent the instrument from rotating along its axis when assembled. In some implementations, the base and the surgical instrument are configured such that only surfaces 502, 504, and 506 come in contact with the surgical instrument when inserted therein. This may allow the surgical instrument to be fully constrained in space.

The base 500 may include a first channel 510 having an interior surface sized and shaped to accommodate a tightening screw configured to securely attach the base 500 directly or indirectly (e.g, via a tool holder) to a robotic arm of the robotic surgical system. The tightening screw may be placed inside the first channel 510 and extend through the opposite side of the base where it engages the robotic arm (e.g., threads).

The base 500 may include a second channel 508 having an interior surface with a tapered cylindrical shape sized to accommodate a surgical instrument therethrough such that movement of the surgical instrument is constrained in all directions except along an axis defined by the second channel surface 508. The first channel 510 and the second channel 508 may intersect.

Figure 9A:
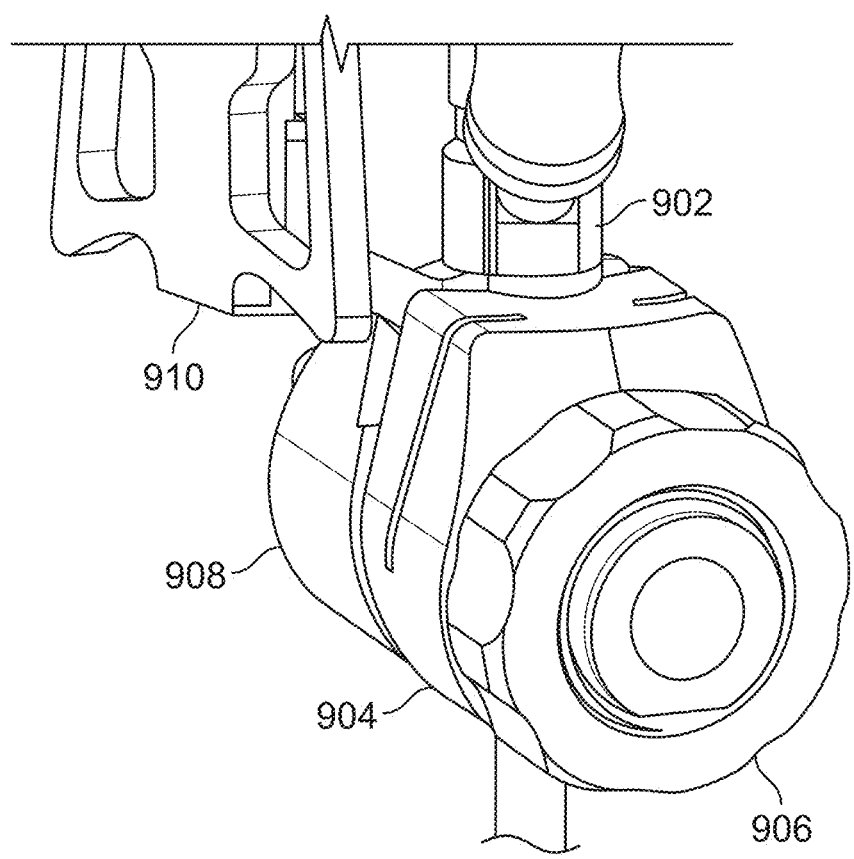
FIGS. 9A-B are illustrations of an example instrument holder with an instrument and a nut for securing the instrument in the holder.

FIG. 6A is an illustration of an example surgical instrument holder before a clamp is installed. FIG. 6B is an illustration of an example surgical instrument holder with a clamp inserted and positioned against the instrument. The clamp 604 may be configured to engage the surgical instrument 606 and/or a navigation marker 608 when the surgical instrument 606 is placed through the second channel such that the surgical instrument is securely held between the clamp 604 and the base 602 upon tightening of a nut (e.g., nut 906 as shown in FIG. 9A). The clamp 604 may include a channel having an interior surface shaped and sized to accommodate the first channel 610 sliding therethrough.

Figure 7:
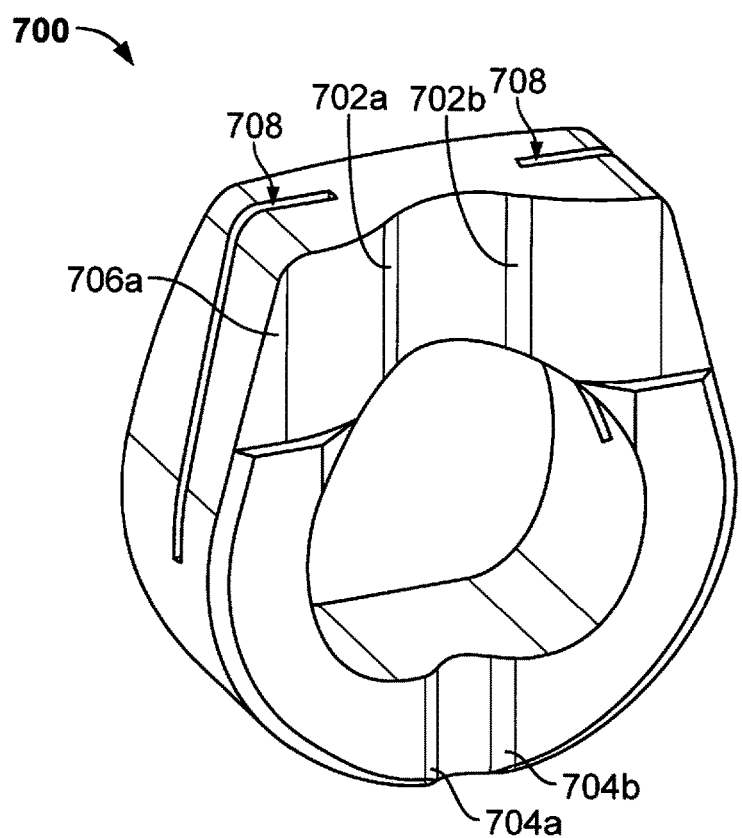
FIG. 7 is an illustration of an example clamp from the guide-side of the clamp.

FIG. 7 is an illustration of an example clamp 700 from the guide-side of the clamp 700. The clamp 700 may include one or more tapered curved surface (e.g., 702 & 704) configured to be engaged by a surgical instrument when the surgical instrument is secured in the second channel (e.g., 508 as shown in FIG. 5A). The tapered curved surface may include four surfaces 702a-b and 704a-b (e.g., four flat surfaces) forming two "V" shapes (shaded) that come in contact with the surgical instrument when inserted in the second channel (e.g., 508 as shown in FIG. 5A). Surfaces 706a and/or 706b may come in contact with the navigation marker's attachment to hold it between the clamp 700 and the base (e.g., 500 in FIG. 5A). In some implementations, the navigation marker may be mounted in two different orientations, one in which it contacts surface 706a and another in which it contacts surface 706b when the surgical instrument is inserted in the second channel. The clamp 700 may include one or more slits 708 configured to allow a body of the clamp to elastically deform upon tightening of the nut. This may compensate for dimension variations in, among other things, surgical tools inserted into the surgical instrument holder.

Figure 8:
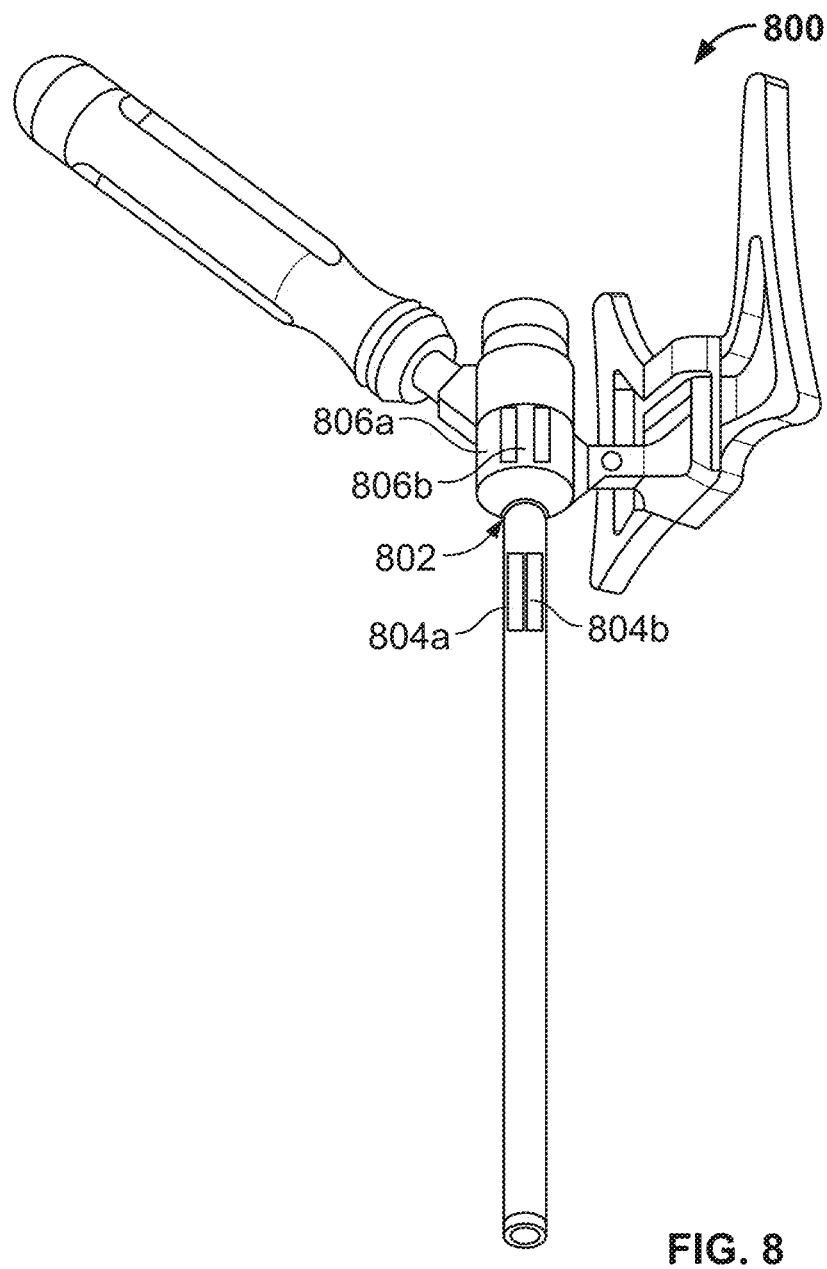
FIG. 8 is an illustration of an example surgical instrument.

FIG. 8 is an illustration of an example surgical instrument 800. The surfaces of the surgical instrument that contact the surgical instrument holder are shown in FIG. 8. In some implementations, surface 802 of the surgical instrument contacts surface 504 of the surgical instrument holder 500 as shown in FIG. 5A when the surgical instrument holder is inserted in the second channel (e.g., 508 in FIG. 5A). In some implementations, surface 806a-b of the surgical instrument contacts surface 502a-b of the surgical instrument holder 500 as shown in FIG. 5A when the surgical instrument holder is inserted in the second channel (e.g., 508 in FIG. 5A). In some implementations, surface 804a-b of the surgical instrument contacts surface 502c-d of the surgical instrument holder 500 as shown in FIG. 5A when the surgical instrument holder is inserted in the second channel (e.g., 508 in FIG. 5A). This configuration may allow for a very stable holding of the instrument in the holder. Additionally, this configuration may prevent a user from inserting the clamp in a wrong orientation with respect to the base (e.g., given the difference in size and/or shape of surface 804 and 806 where the clamp contacts the instrument).

Figure 9B:
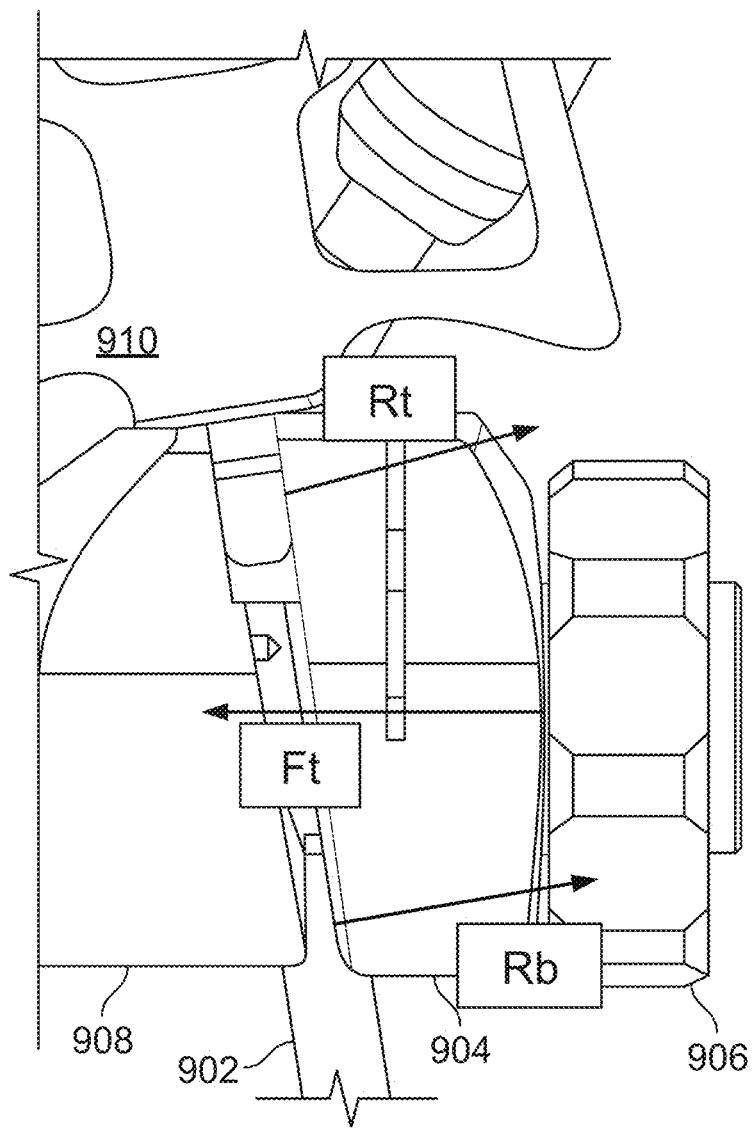

FIGS. 9A-B are illustrations of an example instrument holder with an instrument 902 and a nut 906 for securing the instrument 902 in the holder. An instrument 902 may be secured between a base 908 and a clamp 904. In some implementations, a navigation marker 910 is secured between the base 908 and the clamp 904. A nut 906 may be tightened against the clamp 904 to press the instrument 902 (and/or navigation marker 910) securely between the clamp 904 and the base 908. The nut 906 may be configured to engage threads on an exterior surface of the first channel (e.g., 510 as shown in FIG. 5A) and a cambered surface of the clamp.

In order to balance the tightening force Ft of the nut 906 between the bottom reaction force Rb and the top reaction force Rt as illustrated in FIG. 9B, the nut 906, in some implementations, comes in contact with a cambered surface on the clamp 904 forming only a horizontal line of contact instead of a full surface. This horizontal line of contact may allow the clamp 904 to slightly tilt to accommodate for dimensional variations. This isostatic designs may allow for decreasing internal forces and thus optimizing tightening force Rt and Rd.

The navigation marker may be, for example, a navigation tracker such as the Dedicated NavLock™ tracker from Medtronic, Inc. of Minneapolis, Minn. The navigation marker may be used by a navigation camera to track the surgical instrument. In some implementations, a computing system of the robotic surgical system tracks the position of the patient and the surgical tool, for example using tracking module. The computing system receives images of the patient, surgical tool position, and end effector positions from a tracking detector. In some implementations, images of the patient are received from a digital 3D scanner. Tracking module, for example, may calculate the position of the surgical tool and the patient in real time. In an implementation, tracking module may track the position of the surgical tool and the patient in free space. In another implementation, tracking module may track the position of the surgical tool and the patient with relation to each other. In an implementation tracking module may identify, from the images received from the tracking detector, the portion of the patient to be operated on and the surgical tool and track these identified objects. In another implementation, tracking module may track markers (e.g., navigation markers attached to the portion of the patient to be operated on and the surgical tool. Tracking module may identify the markers from images received from tracking detector and identify that these markers are attached to the patient and to the surgical tool and accordingly, track the patient position and surgical tool position.

Figure 10A:
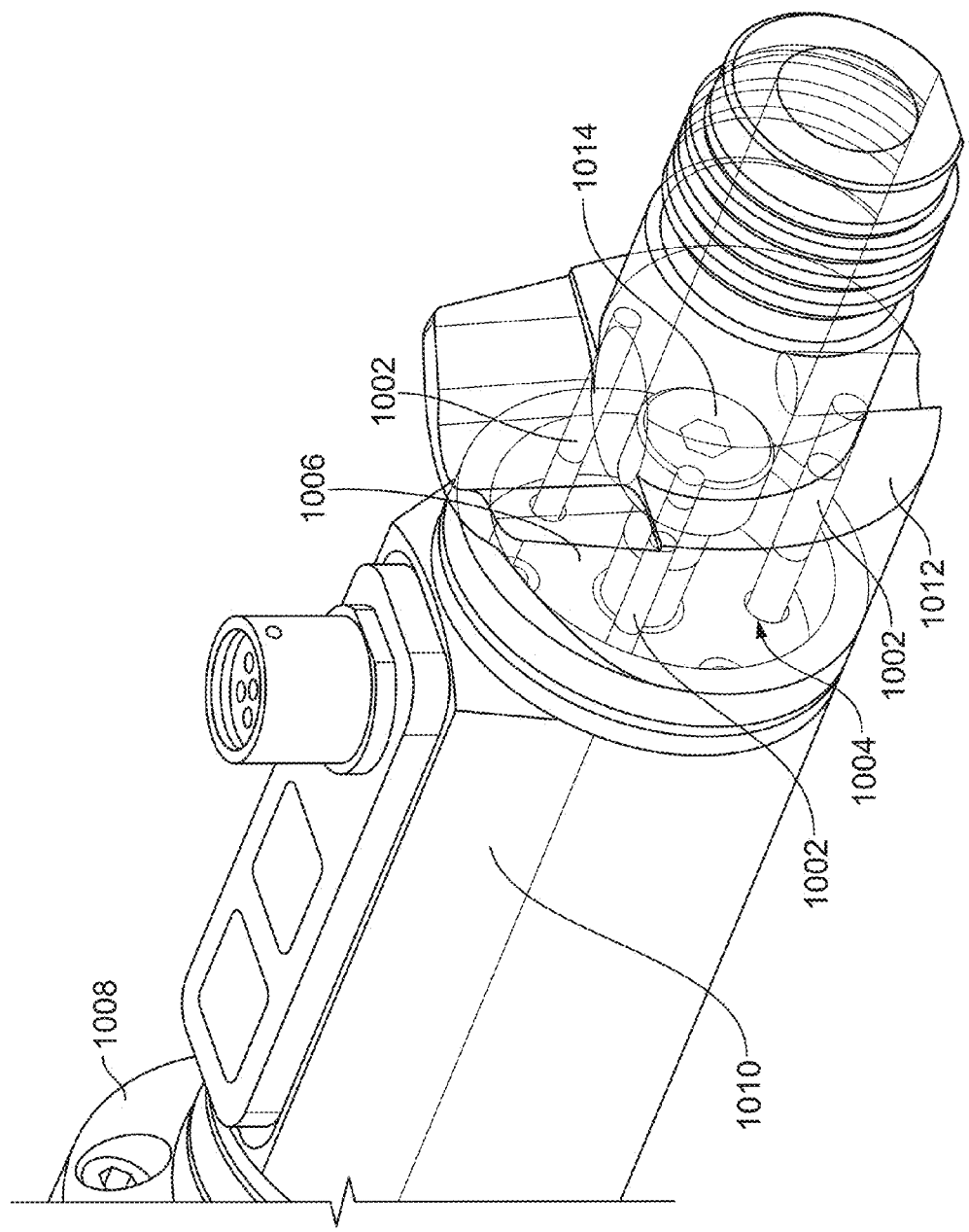

FIGS. 10A-B are illustrations of a system for securing the instrument holder on the robotic arm. In some implementations, the instrument holder needs to be sterilized (e.g., in autoclave). The disclosed instrument holder may be easily installed and removed from the robotic system without deteriorating localization precision as well as attachment rigidity. Localization precision may be achieved by, for example, three localization pins 1002 inserted into the base. A different number of localization pins 1002 may be used (e.g., 1 to 5 pins). The pins 1002 may come in contact with oblong openings 1004 in a thin localization plate 1006 precisely held on the robotic arm 1008 (e.g., held on the tool holder's body 1010). The instrument holder's base 1012 may be localized on the robotic arm 1008 (e.g., held on the tool holder's body 1010) using pins 1002 that come in contact with oblong openings 1004 in a localization plate 1006 precisely held on the robot 1008. A screw 1014 may be tightened directly into the robot 1008 to rigidly attached the instrument holder's base 1012 to the robot 1008. FIG. 10B illustrates a front view of an example localization plate 1006. The one or more pins 1002 may be inserted into the base such that the one or more pins 1002, upon mechanically coupling the base to the robotic arm, engage one or more openings 1004 in a robotic arm 1008 (e.g., in a localization plate 1006 of the robotic arm 1008) thereby precisely locating the surgical instrument holder relative to the robotic arm 1008 (e.g., the one or more openings 1004 may be wider than the one or more pins and the one or more openings may taper long their lengths).

Figure 11:
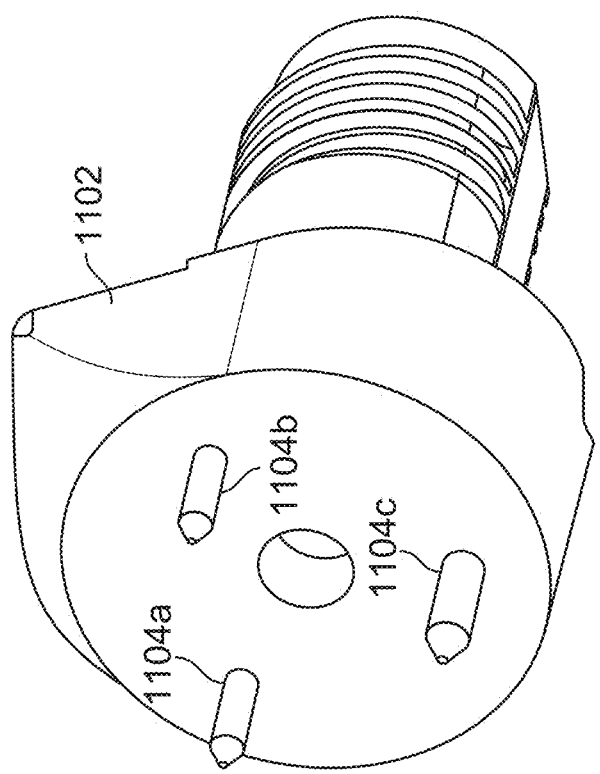
FIG. 11 is an illustration of an example base of an instrument holder.

FIG. 11 is an illustration of an example base 1102 of an instrument holder with pins 1104a-c inserted into the base 1102. The base 1102 may be configured to be mechanically coupled to a robotic arm of the robotic surgical system. The base 1102 may include one or more pins 1104 (e.g., three pins 1104a-c) inserted into the base 1102 such that the one or more pins 1104, upon mechanically coupling the base 1102 to the robotic arm, engage one or more openings in a tool support (e.g., in a localization plate of the robotic arm) thereby precisely locating the surgical instrument holder relative to the robotic arm.

Figure 12A:
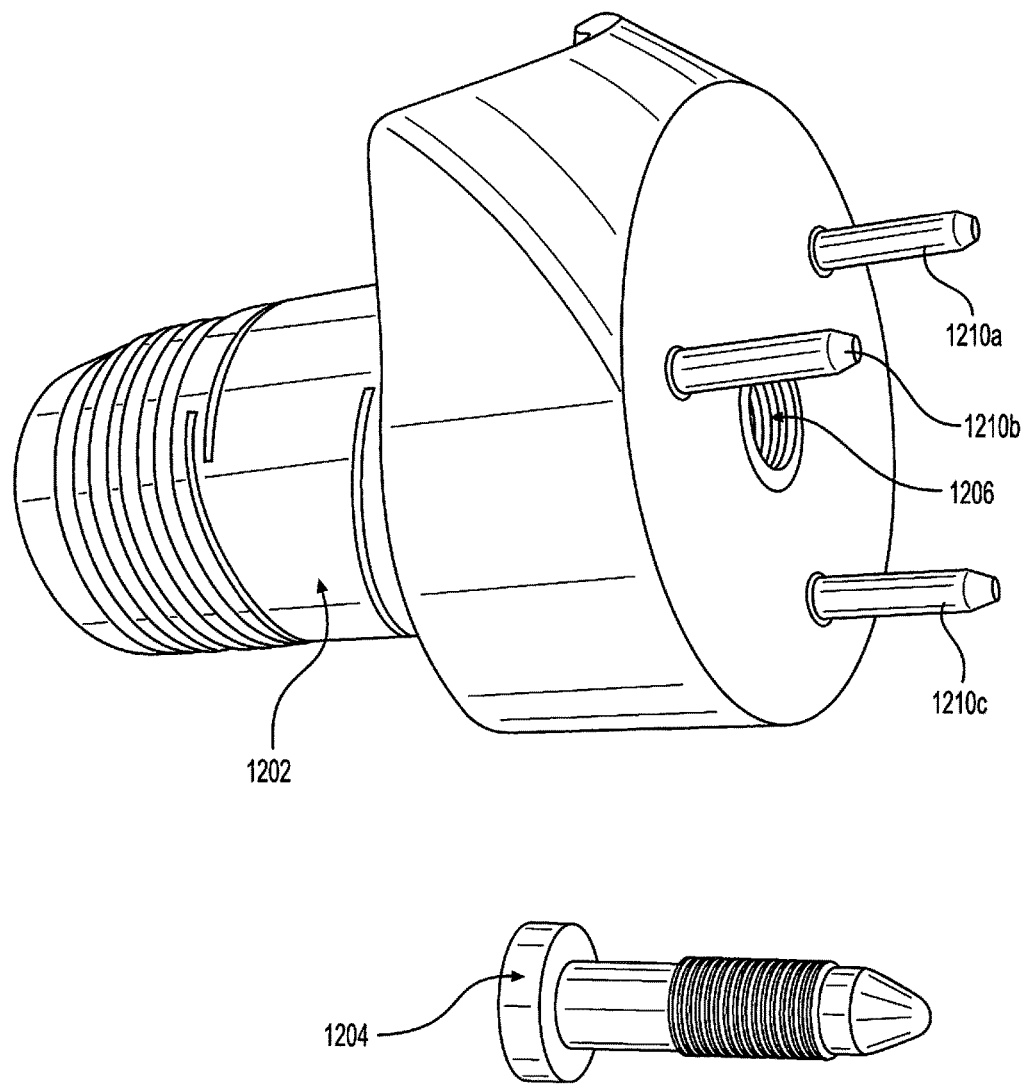
FIG. 12A is an illustration of a clamp base and torque screw, in accordance with an embodiment of the invention.

FIG. 12A is an illustration of a clamp base 1202 and torque screw 1204. In some implementations, a threaded bushing 1206 is press fitted into the clamp base 1202. The torque screw 1204 is made of metal such that it provides a strong attachment to the robot and satisfies the cleaning and sterilization requirements. The threads on the torque screw 1204 engage the threaded bushing 1206 that is press fitted into the clamp base 1202. As the torque screw 1204 is tightened, the threads on the torque screw 1204 pass through the threaded bushing 1206 such that the end of the torque screw 1204 closest to the torque screw head (i.e., the portion that has a smaller diameter and no threads) resides in the threaded bushing 1206 (e.g., somewhat loosely since there are no threads). The advantage here is the torque screw 1204 and clamp base assembly 1202 can then be mounted on the robot without the risk of losing the torque screw 1204 during assembly as the torque screw 1204 cannot slide out of the threaded bushing 1206 as the threads on the torque screw 1204 will contract the threaded bushing 1206 (i.e., thereby preventing the torque screw 1204 from sliding out of the bushing 1206 without unscrewing the torque 1204 from the bushing 1206). The clamp base 1202 in this example includes three localization pins 1210a-c as described above.

Figure 12B:
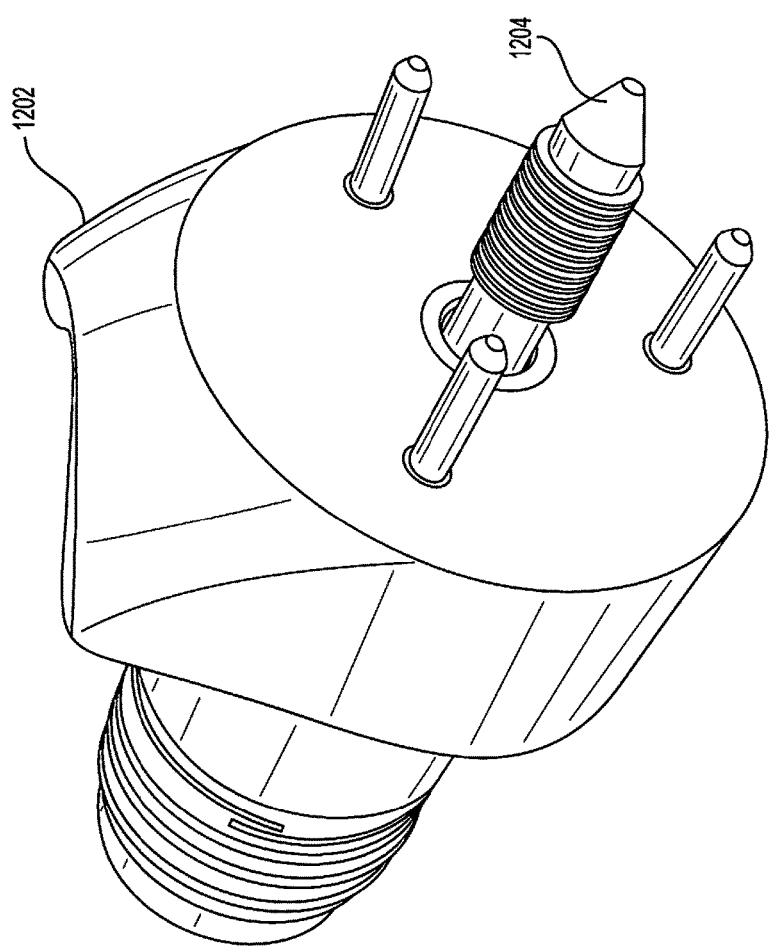
FIG. 12B is an illustration of a clamp base and torque screw, in accordance with an embodiment of the invention.

FIG. 12B is an illustration of a clamp base 1202 with a torque screw 1204 fully inserted into the threaded bushing 1206. The end of the torque screw 1204 has a smaller diameter in order to allow tightening it on the tool holder body as well as providing a gap between the torque screw 1204 and clamp base 1202 for cleaning.

Figure 12C:
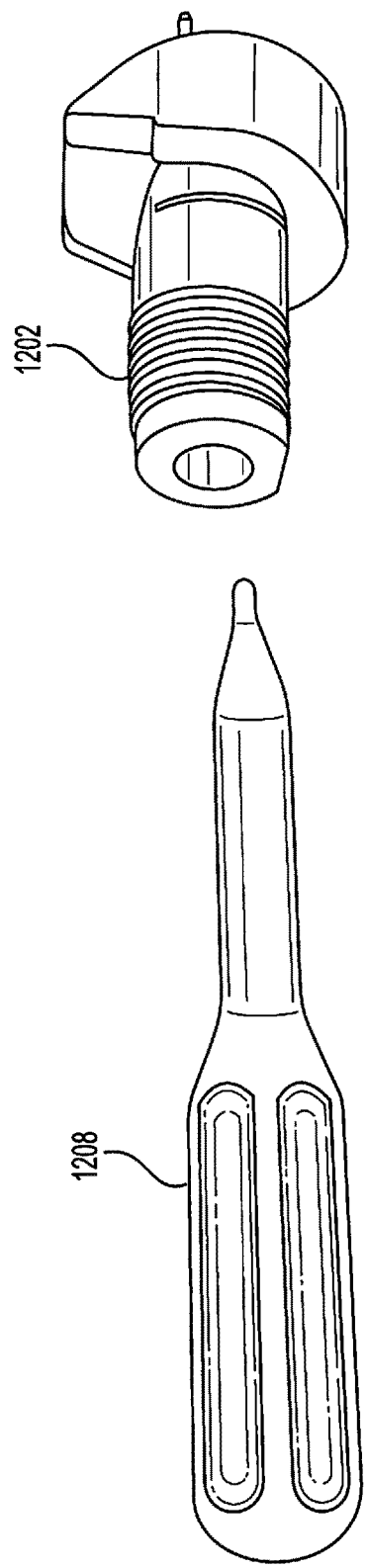
FIG. 12C is an illustration of a clamp base and screw driver, in accordance with an embodiment of the invention.

FIG. 12C is an illustration of a clamp base 1202 and screw driver 1208. For tightening the torque screw 1204, a screw driver 1208 is designed with a shaft diameter close to the inner diameter of the clamp base 1202. Therefore, the screw driver 1208 is guided by the clamp base 1202 once it's inserted into the clamp base 1202 and this simplifies fitting the tip of the screwdriver 1208 on the head of the screw 1204.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A surgical instrument holder for use with a robotic surgical system, the surgical instrument holder comprising:
   a base configured to be mechanically coupled to a robotic arm of the robotic surgical system, the base comprising:
      a first channel having an interior surface sized and shaped to accommodate a tightening screw configured to securely attach the base directly or indirectly to a robotic arm of the robotic surgical system,
      a second channel having an interior surface with a tapered cylindrical shape sized to accommodate a surgical instrument therethrough such that movement of the surgical instrument is constrained in all directions except along an axis defined by the second channel surface,
      a first tapered curved surface extending along the axis of the second channel configured to be engaged by a surgical instrument when the surgical instrument is secured in the second channel, wherein first channel and the second channel intersect, and
      one or more pins inserted into the base such that the one or more pins, upon mechanically coupling the base to the robotic arm, engage one or more openings in a tool support thereby precisely locating the surgical instrument holder relative to the robotic arm; and
   a clamp configured to engage the surgical instrument when placed through the second channel such that the surgical instrument is securely held between the clamp and the base upon tightening of a nut.

2. The surgical instrument holder of claim 1, wherein the base comprises a threaded bushing having an interior surface.

3. The surgical instrument holder of claim 2, wherein the first channel passes through interior surface of the threaded bushing and the interior surface of the threaded bushing is threaded such that the threads on the tightening screw engage the threads on the threaded bushing as the tightening screw is inserted through the threaded bushing.

4. The surgical instrument holder of claim 1, wherein the tightening screw comprises:
   a tip on a proximate end of a screw body;
   a head on a distal end of the screw body; and
   threads along a portion of the screw body.

5. The surgical instrument holder of claim 4, wherein the threads along the portion of the screw body are along a portion of the screw body closest to the tip of the tightening screw.

6. The surgical instrument holder of claim 5, wherein the portion of the screw body closest to the head is smooth such that the tightening screw is loosely held in place by the threaded bushing when the tightening screw is fully inserted into the threaded bushing.

7. The surgical instrument holder of claim 1, the clamp comprising:
   a third channel having an interior surface shaped and sized to accommodate the first channel sliding therethrough;
   a second tapered curved surface configured to be engaged by a surgical instrument when the surgical instrument is secured in the second channel; and
   one or more slits configured to allow a body of the clamp to elastically deform upon tightening of the nut, wherein the nut is configured to engage threads on an exterior surface of the first channel and a cambered surface of the clamp.

8. The surgical instrument holder of claim 1, wherein the one or more openings are one or more oblong openings.

9. The surgical instrument holder of claim 1, wherein the one or more pins comprise three pins.

10. The surgical instrument holder of claim 1, wherein the surgical instrument is an instrument guide configured to receive a second surgical instrument therethrough, the second surgical instrument comprising a member selected from the group consisting of: a drill bit, tap, screw driver, and awl.

11. The surgical instrument holder of claim 10, wherein the instrument guide is a drill guide.

12. The surgical instrument holder of claim 1, wherein the robotic surgical system is for use in spinal surgery.

13. The surgical instrument holder of claim 1, wherein instrument holder is configured such that a navigation marker is securely held between the clamp the base upon placing the navigation marker between the clamp and the base and tightening the nut.

14. The surgical instrument holder of claim 13, wherein the navigation marker is used by a navigation camera to track the surgical instrument.

15. The surgical instrument holder of claim 1, wherein the tool support is a localization plate of the robotic arm.

16. The surgical instrument holder of claim 1, wherein the one or more openings are wider than the one or more pins and the one or more openings taper long their lengths.

17. The surgical instrument holder of claim 1, wherein an exterior surface of the first channel is threaded to securely accommodate the nut such that surgical instrument is securely held between the clamp the base upon placing the surgical instrument in the second channel and tightening the nut.

* * * * *